United States Patent
Lindor

(10) Patent No.: US 6,297,229 B1
(45) Date of Patent: Oct. 2, 2001

(54) USE OF URSODEOXYCHOLIC ACID TO TREAT NONALCOHOLIC STEATOHEPATITIS

(75) Inventor: Keith D. Lindor, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 08/339,084

(22) Filed: Nov. 14, 1994

(51) Int. Cl.$^7$ ................................................. A61K 31/56
(52) U.S. Cl. .......................... 514/182; 514/893; 514/894
(58) Field of Search ..................................... 514/182, 893, 514/894

(56) References Cited

PUBLICATIONS

W.H. Bachrach et al., "Ursodeoxycholic Acid in the Treatment of Cholesterol Cholelithiasis, Part II," *Digestive Diseases and Sciences*, 27, 833–858 (Sep. 1982).

Y. Calmus et al., "Hepatic Expression of Class I and Class II Major Histocompatibility Complex Molecules in Primary Biliary Cirrhosis: Effect of Ursodeoxycholic Acid," *Hepatology*, 11, 12–15 (1990).

J.S. Crippin et al., "Ursodeoxycholic Acid Inhibits Lymphocyte Blastogenesis in a Cholestatic Model," *Gastroenterology*, 98, A578 (May 1990). (Abstract).

J.M. Laurin et al., "Ursodeoxycholic Acid Improves Indices of Liver Injury in Nonalcoholic Steatohepatitis," *Gastroenterology*, 106, p. A926 (Apr. 1994). (Abstract).

U. Leuschner et al., "Gallstone Dissolution with Ursodeoxycholic Acid in Patients with Chronic Active Hepatitis and Two Years Follow–up, A Pilot Study," *Digestive Diseases and Sciences*, 30, 642–649 (Jul. 1985).

J. Ludwig et al., "Nonalcoholic Steatohepatitis," *Mayo Clin. Proc.*, 55, 434–438, (Jul. 1980).

M. Podda et al., "Effect of Different Doses of Ursodeoxycholic Acid in Chronic Liver Disease," *Digestive Disease and Sciences*, 34, 59S–65S (Dec. 1989 Supplement).

R. Poupon et al., "Is Ursodeoxycholic Acid an Effective Treatment for Primary Biliary Cirrhosis?" *The Lancet*, 834–836 (Apr. 11, 1987).

E.E. Powell et al., "The Natural History of Nonalcoholic Steatohepatitis: A Follow–Up Study of Forty–two Patients for Up to 21 Years," *Hepatology*, 11, 74–80 (Jan. 1990).

B.F. Scharschmidt et al., "Hepatocellular Bile Acid Transport and Ursodeoxycholic Acid Hypercholeresis," *Digestive Diseases and Sciences*, 34, 5S–15S (Dec. 1989 Supplement).

J. Schölmerich et al., "Influence of Hydroxylation and Conjugation of Bile Salts on Their Membrane–Damaging Properties—Studies on Isolated Hepatocytes and Lipid Membrane Vesicles," *Hepatology*, 4, 661–666 (1984).

I.R. Wanless et al., "Fatty Liver Hepatitis (Steatohepatitis) and Obesity: An Autopsy Study with Analysis of Risk Factors," *Hepatology*, 12, 1106–1110 (Nov. 1990).

HCAPLUS Abstract 1987: 61224, Shironaga, 1986.*

\* cited by examiner

Primary Examiner—Russell Travers
Assistant Examiner—Shengjun Wang
(74) Attorney, Agent, or Firm—Schwegman, Lundberg, Woessner & Kluth, P.A.

(57) ABSTRACT

A therapeutic method for the treatment of nonalcoholic steatohepatitis is provided, comprising administering to a patient in need of said treatment an effective amount of ursodeoxycholic acid or a pharmaceutically acceptable derivative thereof.

8 Claims, No Drawings

USE OF URSODEOXYCHOLIC ACID TO TREAT NONALCOHOLIC STEATOHEPATITIS

BACKGROUND OF THE INVENTION

Nonalcoholic steatohepatitis (NASH) involves the development of histologic changes in the liver that are comparable to those induced by excessive alcohol intake but in the absence of alcohol abuse. Macrovesicular and/or microvesicular steatosis, lobular and portal inflammation, and occasionally Mallory bodies with fibrosis and cirrhosis characterize NASH. NASH is also commonly associated with hyperlipidemia, obesity, and type II diabetes mellitus. Other clinical conditions characterized by hepatic steatosis and inflammation include excessive fasting, jejunoileal bypass, total parental nutrition, chronic hepatitis C, Wilson's disease, and adverse drug effects such as those from corticosteroids, calcium channel blockers, high dose synthetic estrogens, methotrexate and amiodarone. Thus, the term "nonalcoholic steatohepatitis" can be used to describe those patients who exhibit these biopsy findings, coupled with the absence of (a) significant alcohol consumption, (b) previous surgery for weight loss, (c) history of drug use associated with steatohepatitis, (d) evidence of genetic liver disease or (e) chronic hepatitis C infection. See, J. R. Ludwig et al., *Mayo Clin. Proc.*, 55, 434 (1980) and E. E. Powell et al., *Hepatol.*, 11, 74 (1990).

The pathogenesis of NASH is unknown. A correlation seems to exist between the degree of steatosis and the degree of fibrosis. For example, see I. R. Wanless et al., *Hepatology*, 12, 1106 (1990). Elevated hepatocellular free fatty acids may cause membrane injury with subsequent inflammation, possible cholestasis, and subcellular organelle dysfunction. Cell death and fibrosis follow persistent inflammation, and cirrhosis occurs if the injury continues. Steatohepatitis is now considered an important cause of end-stage liver disease and may be the cause of an unknown number of cases of clyptogenic cirrhosis. See E. E. Powell et al, cited above. Unfortunately, once cirrhosis is established, the only therapeutic modality available is orthotopic liver transplantation. Thus, effective therapy for nonalcoholic steatohepatitis is clearly needed.

SUMMARY OF THE INVENTION

The present invention provides a therapeutic method comprising administering to a human patient afflicted with nonalcoholic steatohepatitis (NASH) an amount of ursodeoxycholic acid (UCDA), a pharmaceutically acceptable ester or a pharmaceutically acceptable salt thereof, which amount is effective to treat said nonalcoholic steatohepatitis. Of the modes of administration, the oral administration of total dosages of about 500–1000 mg/day (adult) of UCDA is preferred. As used herein, the term "treat" is intended to include significant lowering of at least one of the serum enzyme markers, the elevation of which is associated with NASH, or histologic improvement by at least one grade. The clinical condition of the patient treated may be improved, but, as in the case of any progressive pathology, effective treatment also comprises slowing the progression of the condition, as well as halting it completely.

DETAILED DESCRIPTION OF THE INVENTION

Ursodeoxycholic acid (UDCA) has the formula:

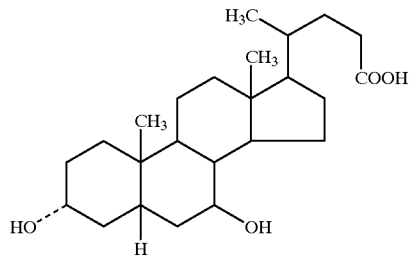

and the full chemical name 17β-(1-methyl-3-carboxypropyl) etiocholane-3α, 7βdiol. No major toxicity is known to be associated with UDCA (W. H. Bachrach et al., *Dig. Dis. Sci.*, 30, 642 (1985)). Thus, pharmaceutically acceptable salts and esters of UDCA include nontoxic esters of the free hydroxyl groups of UDCA with ($C_1$–$C_4$)alkanoic acids such as formic, acetic or propionic acid, phosphate esters of the OH groups, ($C_1$–$C_4$)alkyl esters of the free ($C_{24}$) carboxylic acid group and nontoxic alkali metal, ammonium or amine salts of the free carboxylic acid moiety. This ester and salts can be readily prepared from free UCDA by methods well known to the art. At least the diformate and diacetate esters are known compounds. See, *The Merck Index* (11th ed. 1989) at 1556. UDCA is commercially available in 300 mg hard gelatin capsules as Actigall® from Summit Pharmaceuticals, Summit, N.J., and is prescribed for gallbladder stone dissolution.

It will be further appreciated that the amount of UDCA required for use in treatment will vary not only with the particular form of UDCA selected but also with the route of administration, the severity of the symptoms being treated and the age and condition of the patient and will be ultimately at the discretion of the attendant physician or veterinarian. In general, however, a suitable daily dose will be in the range of from about 5 to about 25 mg/kg, e.g., from about 8–10 mg/kg to about 16–20 mg/kg of bodyweight per day.

Preferably, the amount of ursodeoxycholic acid is administered orally, in single or multiple daily doses, at from about 500–1500 mg total daily doses, i.e., via pharmaceutical unit dosage forms, such as tablets or capsules, which are adapted for oral administration. Prolonged treatment with UDCA is contemplated in accord with the method, involving treatment periods of 1–5 years or longer.

While it is possible that, for use in therapy, a compound of the invention may be administered as the pure acid, it is preferable to present the active ingredient as a pharmaceutical formulation. The invention thus further provides a pharmaceutical formulation comprising a compound of formula (I) or a pharmaceutically acceptable derivative thereof together with one or more pharmaceutically acceptable carriers and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation or insufflation. The formulations may, where appropriate, be conveniently presented in discrete unit dosage form and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulations suitable for oral administration may conveniently be presented as discrete units such as capsules, cachets or tablets, each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

UDCA and its derivatives may also be formulated for parenteral administration (e.g., by injection, for example, bolus injection or continuous intravenous or enteral infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

When desired, the above described formulations adapted to give sustained release of the active ingredient may be employed.

The pharmaceutical compositions according to the invention may also contain other active ingredients such as antimicrobial agents, or preservatives.

The compounds of the invention may also be used in combination with other therapeutic agents and nutritional supplements.

The invention will be further described by reference to the following detail example.

EXAMPLE 1

Twenty-four patients were diagnosed with nonalcoholic steatohepatitis (NASH) at the Mayo Clinic based on a compatible liver biopsy showing >10% steatosis, along with other etiologies of liver disease, including alcoholism excluded by history, serum tests confirming elevated alanine aminotransferase (ALT), and ultrasound. All patients received 12–15 mg/kg/day of UDCA in divided doses. Serum biochemistries, measurement of body weight, lipid profile, and percutaneous liver biopsies were performed at entry and after one year of therapy.

Hepatic steatosis, fibrosis, and inflammation were graded on a scale of 0 (none) and 3 (severe). Other etiologies of liver disease were ruled out by history, serum tests and ultrasound. The mean age of the eight males and sixteen females was 44.1±13.2 years. Obesity (>20% above ideal body weight) was present in 14/241(58%) patients. Nine patients were using oral hypoglycemic agents and/or insulin or had a fasting glucose >150 mg/dl. Three of 24 patients (12.5%) withdrew from the study because of side effects (tinnitus, severe abdominal pain, and diarrhea). Two (8%) were withdrawn secondary to noncompliance; one of whom later required liver transplantation.

The decreases in mean serum alkaline phosphatase (Alk Phos), alanine aminotransferase (ALT), and gamma-glutamyl transpeptidase (GGT) after twelve months of UDCA therapy were significantly different from baseline compared to entry, as shown on Table I (95% C.I.)

TABLE I

|  | Alk Phos | ALT | GGT | Grade of Fat (Mean) |
|---|---|---|---|---|
| Change | −19.5 U/L | −39 U/L | −33.6 U/L | −0.34 |
| 95% C.I. | −0.6 to −38.4 | −16.5 to −61.5 | −18.3 to −48.9 | −0.11 to −0.57 |

There was no significant change in triglycerides, cholesterol, body weight, the grade of fibrosis, or inflammation. The data summarized on Table I demonstrates that treatment of NASH with UDCA for twelve months results in significant improvement in alkaline phosphatase, ALT and GGT levels, which are serum enzymes indicative of liver functions such as cytolysis and a cholestasis. The grade of hepatic steatosis (measured as "grade of fat") also improved (95% C.I.). Six of nineteen patients (32%) also had histologic improvement by one grade or more at twelve months. Thus, UJDCA can provide an effective treatment for UDCA.

All publications are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A therapeutic method for the treatment of nonalcoholic steatohepatitis comprising administering to a human patient in need of such treatment an effective amount of ursodeoxycholic acid, a pharmaceutically acceptable salt thereof or a pharmaceutically acceptable ester thereof.

2. The method of claim 1 wherein an effective amount of ursodeoxycholic acid is administered in combination with a pharmaceutically acceptable carrier.

3. The method of claim 2 wherein the amount of ursodeoxycholic acid is administered in a pharmaceutical unit dosage form which is adapted for oral administration.

4. The method of claim 3 wherein the unit dosage form is a tablet or a capsule.

5. The method of claim 1 wherein the amount of ursodeoxycholic acid is administered in a daily dose of from about 5 mg/kg to about 25 mg/kg.

6. The method of claim 2 wherein the amount of ursodeoxycholic acid is administered in combination with a liquid carrier.

7. The method of claim 6 wherein the combination of ursodeoxycholic acid and said liquid carrier is adapted for parenteral administration.

8. The method of claim 7 wherein the combination of ursodeoxycholic acid and said liquid carrier is adapted for intravenous administration.

* * * * *

UNITED STATES PATENT AND TRADEMARK OFFICE
CERTIFICATE OF CORRECTION

PATENT NO. : 6,297,229 B1
DATED : October 2, 2001
INVENTOR(S) : Keith D. Lindor

It is certified that error appears in the above-identified patent and that said Letters Patent is hereby corrected as shown below:

<u>Column 3,</u>
Line 65, delete "14/241(58%)" and insert -- 14/24/(58%) --, therefor.

<u>Column 4,</u>
Line 31, delete "UJDCA" and inset -- UDCA --, therefor.

Signed and Sealed this

Thirtieth Day of April, 2002

Attest:

Attesting Officer

JAMES E. ROGAN
Director of the United States Patent and Trademark Office